United States Patent [19]
Keim

[11] Patent Number: 6,008,438
[45] Date of Patent: Dec. 28, 1999

[54] COTTON CULTIVAR DP 2379

[75] Inventor: Don Lee Keim, Leland, Miss.

[73] Assignee: Agripio Seeds, Inc., Shawnee Mission, Kans.

[21] Appl. No.: 09/042,999

[22] Filed: Mar. 17, 1998

[51] Int. Cl.$^6$ ............................. A01H 5/00; A01H 4/00; A01H 1/00; A01H 5/10; A01G 7/00
[52] U.S. Cl. ..................... 800/314; 800/260; 435/427
[58] Field of Search .................... 800/314, 260; 435/427

[56] References Cited

PUBLICATIONS

W.R. Fehr, Principles of Cultivar Development: vol. 1, Theory and Technique, McGraw–Hill, USA, pp. 31–33, 1987.
R.W. Allard, Plant Breeding, John Wiley & Sons, USA, p. 55, 1960.
D.D. Davis, 'Registration of Five Upland–type Parental A–and B–lines for Hybrid Cotton,' Crop Science, vol. 33, No. 6, p. 1426, 1993.
McCall et al, 'Genotype Environment Interaction Study of Lock Tenacity in Upland Cotton Gossypium–hirsutum', Crop Science, vol. 22, No. 4, p. 794–797, 1982.
Plant Variety Protection Certificate No. 8100143 for Cotton Cultivar Deltapine Acala 90 Jun. 17, 1982.
Plant Variety Protection Certificate No. 8600087 for Cotton Paymaster HS26 Jun. 30, 1992.

*Primary Examiner*—David T. Fox
*Assistant Examiner*—Anne Marie Grünberg
*Attorney, Agent, or Firm*—Rothwell, Figg, Ernst & Kurz

[57] ABSTRACT

A novel cotton cultivar, designated DP 2379, is disclosed. The invention relates to the seeds of cotton cultivar DP 2379, to the plants of cotton DP 2379 and to methods for producing a cotton plant by crossing the cultivar DP 2379 with itself or another cotton variety. The invention further relates to hybrid cotton seeds and plants produced by crossing the cultivar DP 2379 with another cotton cultivar.

15 Claims, No Drawings

6,008,438

COTTON CULTIVAR DP 2379

BACKGROUND OF THE INVENTION

The present invention relates to a new and distinctive cotton cultivar, designated DP 2379. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. In cotton, the important traits include higher fiber (lint) yield, earlier maturity, improved fiber quality, resistance to diseases and insects, tolerance to drought and heat, and improved agronomic traits.

Pureline cultivars, as generally used in cotton, are commonly bred by hybridization of two or more parents followed by selection. The complexity of inheritance, the breeding objectives and the available resources influence the breeding method. Pedigree breeding, recurrent selection breeding and backcross breeding are breeding methods commonly used in self pollinated crops such as cotton. These methods refer to the manner in which breeding pools or populations are made in order to combine desirable traits from two or more cultivars or various broad-based sources. The procedures commonly used for selection of desirable individuals or populations of individuals are called mass selection, plant-to-row selection and single seed descent or modified single seed descent. One, or a combination of these selection methods, can be used in the development of a cultivar from a breeding population.

Pedigree breeding is primarily used to combine favorable genes into a totally new cultivar that is different in many traits than either parent used in the original cross. It is commonly used for the improvement of self-pollinating crops. Two parents which possess favorable, complementary traits are crossed to produce an $F_1$ (filial generation 1). An $F_2$ population is produced by selfing $F_1$ plants. Selection of desirable individual plants may begin as early as the $F_2$ generation wherein maximum gene segregation occurs. Individual plant selection can occur for one or more generations. Successively, seed from each selected plant can be planted in individual, identified rows or hills, known as progeny rows or progeny hills, to evaluate the line and to increase the seed quantity, or, to further select individual plants. Once a progeny row or progeny hill is selected as having desirable traits it becomes what is known as a breeding line that is specifically identifiable from other breeding lines that were derived from the same original population. At an advanced generation (i.e., $F_5$ or higher) seed of individual lines are evaluated in replicated testing. At an advanced stage the best lines or a mixture of phenotypically similar lines from the same original cross are tested for potential release as new cultivars.

Descriptions of other breeding methods that are commonly used for different traits and crops can be found in one of several reference books (e.g., Allard, 1960; Simmonds, 1979; Sneep, et al. 1979; Fehr, 1987).

The single seed descent procedure in the strict sense refers to planting a segregating population, harvesting one seed from every plant, and combining these seeds into a bulk which is planted the next generation. When the population has been advanced to the desired level of inbreeding, the plants from which lines are derived will each trace to different $F_2$ individuals. Primary advantages of the seed descent procedures are to delay selection until a high level of homozygosity (e.g., lack of gene segregation) is achieved in individual plants, and to move through these early generations quickly, usually through using winter nurseries.

The modified single seed descent procedures involve harvesting multiple seed (i.e., a single lock or a simple boll) from each plant in a population and combining them to form a bulk. Part of the bulk is used to plant the next generation and part is put in reserve. This procedure has been used to save labor at harvest and to maintain adequate seed quantities of the population.

Selection for desirable traits can occur at any segregating generation ($F_2$ and above). Selection pressure is exerted on a population by growing the population in an environment where the desired trait is maximally expressed and the individuals or lines possessing the trait can be identified. For instance, selection can occur for disease resistance when the plants or lines are grown in natural or artificially-induced disease environments, and the breeder selects only those individuals having little or no disease and are thus assumed to be resistant.

Promising advanced breeding lines are thoroughly tested and compared to popular cultivars in environments representative of the commercial target area(s) for three or more years. The best lines having superiority over the popular cultivars are candidates to become new commercial cultivars. Those lines still deficient in a few traits are discarded or utilized as parents to produce new populations for further selection.

These processes, which lead to the final step of marketing and distribution, usually take from seven to twelve years from the time the first cross is made. Therefor, development of new cultivars is a time-consuming process that requires precise forward planning, efficient use of resources, and a minimum of changes in direction.

A most difficult task is the identification of individuals that are genetically superior because, for most traits the true genotypic value is masked by other confounding plant traits or environmental factors. One method of identifying a superior plant is to observe its performance relative to other experimental lines and widely grown standard cultivars. For many traits a single observation is inconclusive, and replicated observations over time and space are required to provide a good estimate of a line's genetic worth.

The goal of a commercial cotton breeding program is to develop new, unique and superior cotton cultivars. The breeder initially selects and crosses two or more parental lines, followed by generation advancement and selection, thus producing many new genetic combinations. The breeder can theoretically generate billions of different genetic combinations via this procedure. The breeder has no direct control over which genetic combinations will arise in the limited population size which is grown. Therefore, two breeders will never develop the same line having the same traits.

Each year, the plant breeder selects the germplasm to advance to the next generation. This germplasm is grown under unique and different geographical, climatic and soil conditions, and further selections are then made, during and at the end of the growing season. The lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce, with any reasonable likelihood, the same cultivar twice by using the exact same original parents and the same selection techniques. This unpredictability results in the expenditure of large amounts of research moneys to develop superior new cotton cultivars.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, and the grower, processor and consumer; for special advertising and marketing and commercial production practices, and new product utilization. The testing preceding the release of a new cultivar should take into consideration research and development costs as well as technical superiority of the final cultivar. For seed-propagated cultivars, it must be feasible to produce seed easily and economically.

Cotton, *Gossypium hirsutum,* is an important and valuable field crop. Thus, a continuing goal of plant breeders is to develop stable, high yielding cotton cultivars that are agronomically sound. The reasons for this goal are obviously to maximize the amount and quality of the fiber produced on the land used and to supply fiber, oil and food for animals and humans. To accomplish this goal, the cotton breeder must select and develop plants that have the traits that result in superior cultivars.

The development of new cotton cultivars requires the evaluation and selection of parents and the crossing of these parents. The lack of predictable success of a given cross requires that a breeder, in any given year, make several crosses with the same or different breeding objectives.

The cotton flower is monecious in that the male and female structures are in the same flower. The crossed or hybrid seed is produced by manual crosses between selected parents. Floral buds of the parent that is to be the female are emasculated prior to the opening of the flower by manual removal of the male anthers. At flowering, the pollen from flowers of the parent plants designated as male, are manually placed on the stigma of the previous emasculated flower. Seed developed from the cross is known as first generation ($F_1$) hybrid seed. Planting of this seed produces $F_1$ hybrid plants of which half their genetic component is from the female parent and half from the male parent. Segregation of genes begins at meiosis thus producing second generation ($F_2$) seed. Assuming multiple genetic differences between the original parents, each $F_2$ seed has a unique combination of genes.

SUMMARY OF THE INVENTION

According to the invention, there is provided a novel cotton cultivar, designated DP 2379. This invention thus relates to the seeds of cotton cultivar DP 2379, to the plants of cotton cultivar DP 2379 and to methods for producing a cotton plant by crossing the cotton DP 2379 with itself or another cotton line.

DEFINITIONS

In the description and tables which follow, a number of terms are used. In order to provide a clear and consistent understanding of the specification and claims, including the scope to be given such terms, the following definitions are provided:

Lint Yield. As used herein, the term "lint yield" is defined as the measure of the quantity of fiber produced on a given unit of land. Presented below in pounds per acre.

Lint Percent. As used herein, the term "lint percent" is defined as the lint (fiber) fraction of seed cotton (lint and seed).

Gin Turnout. As used herein, the term "gin turnout" is defined as a fraction of lint in a machine harvested sample of seed cotton (lint, seed, and trash).

Fiber Length. As used herein, the term "fiber length" is defined as 2.5% span length in inches of fiber as measured by High Volume Instrumentation (HVI).

Uniformity Ratio. As used herein, the term "uniformity ratio" is defined as a measure of the relative length uniformity of a bundle of fibers as measured by HVI.

Micronaire. As used herein, the term "micronaire" is defined as a measure of the fineness of the fiber. Within a cotton cultivar, micronaire is also a measure of maturity. Micronaire differences are governed by changes in perimeter or in cell wall thickness, or by changes in both. Within a variety, cotton perimeter is fairly constant and maturity will cause a change in micronaire. Consequently, micronaire has a high correlation with maturity within a variety of cotton. Maturity is the degree of development of cell wall thickness. Micronaire may not have a good correlation with maturity between varieties of cotton having different fiber perimeter. Micronaire values range from about 2.0 to 6.0:

| | | |
|---|---|---|
| Below 2.9 | Very fine | Possible small perimeter but mature (good fiber), or large perimeter but immature (bad fiber). |
| 2.9 to 3.7 | Fine | Various degrees of maturity and/or perimeter. |
| 3.8 to 4.6 | Average | Average degree of maturity and/or perimeter. |
| 4.7 to 5.5 | Coarse | Usually fully developed (mature), but larger perimeter. |
| 5.6+ | Very coarse | Fully developed, large-perimeter fiber. |

Fiber Strength (T1). As used herein, the term "fiber strength" is defined as the force required to break a bundle of fibers as measured in grams per millitex on the HVI.

Fiber Elongation (E1). As used herein, the term "fiber elongation" is defined as the measure of elasticity of a bundle of fibers as measured by HVI.

Plant Height. As used herein, the term "plant height" is defined as the average height in inches of a group of plants.

Stringout Rating (storm resistance). As used herein, the term "stringout rating" is defined as a visual rating prior to harvest of the relative looseness of the seed cotton held in the boll structure on the plant.

Maturity Rating. As used herein, the term "maturity rating" is defined as a visual rating near harvest on the amount of opened bolls on the plant.

Vegetative Nodes. As used herein, the term "vegetative nodes" is defined as the number of nodes from the cotyledonary node to the first fruiting branch on the main stem of the plant.

Fruiting Nodes. As used herein, the term "fruiting nodes" is defined as the number of nodes on the main stem from which arise branches which bear fruit or bolls.

DETAILED DESCRIPTION OF THE INVENTION

Cotton cultivar DP 2379 has superior characteristics and was developed from the cross C1771 B-1×Deltapine Acala 90 made in 1989. C1771 B-1 is a single plant selection from the variety DC81. Plants were advanced from the $F_2$ to $F_3$ stage by the modified single seed descent method. DP 2379 was derived from a single $F_3$ plant in 1991 which was designated breeding line DC81-1/AC90.-79. Progeny row evaluation and selection occurred in 1992. Performance evaluation began in 1993 on the Texas High Plains in replicated tests. In testing from 1993 through 1996, DP 2379 has indicated outstanding lint yield performance.

DP 2379 has superior lint yields to cultivars of similar maturity and adaptation type. It has excellent agronomic characteristics, including storm resistance.

The criteria used to select in various generations include: lint yield, lint turnout, fiber characteristics, maturity, storm resistance, disease tolerance, early season vigor.

The cultivar has shown uniformity and stability to the traits, as described in the following variety description information. It has been advanced a sufficient number of generations with careful attention to uniformity of plant type. The line has been increased with continued observation for uniformity.

Cotton cultivar DP 2379 has the following morphologic and other characteristics.

| VARIETY DESCRIPTION INFORMATION | |
|---|---|
| Species: | *Gossypium hirsutum* L. |
| Areas of Adaptation: | High Plains of Texas and New Mexico Central Texas and Southwest Oklahoma Gulf Coast area of Texas |
| General: | |
| Plant Habit | Intermediate |
| Foliage | Intermediate |
| Stem Lodging | Erect |
| Fruiting Branch | Normal |
| Growth | Intermediate |
| Leaf Color | Dark green |
| Boll Shape | Length more than width |
| Boll Breadth | Broadest at middle |
| Maturity: | |
| Date of 50% open bolls | August 20 |
| Plant: | |
| 1st Fruiting Branch (from cotyledonary node) | 25.8 cm |
| No. of Nodes to 1st Fruiting Branch (Excluding cotyledonary node) | 4.4 |
| Mature Plant Height (from cotyledonary node to terminal) | 91.6 cm |
| Leaf (Upper most, fully expanded leaf): | |
| Type | Normal |
| Pubescence | Sparse 55%; light 30%, medium 15% |
| Nectaries | Present |
| Stem Pubescence: | Intermediate |
| Glands: | |
| Leaf | Normal |
| Stem | Normal |
| Calyx Lobe | Absent |

| VARIETY DESCRIPTION INFORMATION | |
|---|---|
| Flower: | |
| Petals | Cream |
| Pollen | Cream |
| Petal Spot | Absent |
| Seed: | |
| Seed Index (g/100, fuzzybasis) | 10.9 |
| Lint Index (g lint/100 seeds) | 6.84 |
| Boll: | |
| Lint Percent - Picked | 36.8 |
| Gin Turnout - Picked | 37.7 |
| Number of Seeds per Boll | 29.1 |
| Grams Seed Cotton per Boll | 5.36 |
| Number of Locules per Boll | 4–5 |
| Boll Type | Stormproof |
| Fiber Properties: | |
| Method | HVI |
| Length | 1.12 inches |
| Uniformity | 83% |
| Strength (T1) | 29.4 g/tex |
| Elongation (E1) | 6.9% |
| Micronaire | 4.7 |
| Diseases: | |
| Fusarium Wilt | Resistant |
| Verticillium Wilt | Moderately resistant |
| Nematodes, Insects and Pests: | |
| Root-Knot Nematode | Moderately resistant |
| Boll Weevil | Susceptible |
| Bollworm | Susceptible |
| Reniform Nematode | Susceptible |
| Lygus | Susceptible |
| Pink Bollworm | Susceptible |
| Tobacco Bud Worm | Susceptible |

This invention is also directed to methods for producing a cotton plant by crossing a first parent cotton plant with a second parent cotton plant, wherein the first or second cotton plant is the cotton plant from the line DP 2379. Further, both first and second parent cotton plants may be from the cultivar DP 2379. Therefore, any methods using the cultivar DP 2379 are part of this invention: selfing, backcrosses, hybrid breeding, and crosses to populations. Any plants produced using cultivar DP 2379 as a parent are within the scope of this invention. As used herein, the term "plant" includes plant cells, plant protoplasts, plant cells of tissue culture from which cotton plants can be regenerated, plant calli, plant clumps, and plant cells that are intact in plants or parts of plants, such as pollen, flowers, seeds, pods, leaves, stems, and the like. Thus, another aspect of this invention is to provide for cells which upon growth and differentiation produce the cultivar DP 2379.

The cultivar DP 2379 is similar to Paymaster HS26. While similar, there are numerous differences including: DP 2379 has a higher lint yield and higher gin turnout, lower fiber uniformity, lower seed weight, taller plants, earlier maturity, fewer days to 50% open, more fruiting nodes and higher percentage of bolls on vegetative branches than Paymaster HS26.

DP 2379 is a stripper-type variety. The stripper varieties as a group are distinguished from all other varieties primarily by a more storm resistant boll type. DP 2379 is different from all other stripper-type varieties in agronomic and fiber traits.

TABLE 1

PVP Tests - 1996

| Name | Lint Yield | Lint % | Mic | Len | Ur | T1 | E1 | So |
|---|---|---|---|---|---|---|---|---|
| Scott, MS - 6SMC138 | | | | | | | | |
| DP2379 | 920 | 35.4 | 4.7 | 1.11 | 82.6 | 30.3 | 6.8 | 2.0 |
| HS26 | 778 | 35.3 | 4.5 | 1.13 | 82.9 | 30.9 | 6.8 | 1.8 |
| DP Acala 90 | 868 | 33.3 | 4.3 | 1.16 | 81.8 | 29.4 | 6.2 | 3.0 |
| Mean | 859 | 35.0 | 4.3 | 1.13 | 82.5 | 30.1 | 6.3 | 2.8 |
| Cv | 9.3 | 2.7 | 4.2 | 3.0 | 1.1 | 3.5 | 2.4 | 15.8 |
| LSD .05 | 94 | 1.1 | 0.2 | 0.04 | 1.0 | 1.2 | 0.2 | 0.5 |
| Casa Grande, AZ - 6PVP243 | | | | | | | | |
| DP2379 | 1320 | 38.0 | 4.6 | 1.15 | 82.1 | 29.7 | 6.2 | 1.7 |
| HS26 | 1160 | 34.5 | 4.5 | 1.17 | 83.6 | 31.1 | 6.1 | 1.2 |
| DP Acala 90 | 1560 | 36.5 | 4.5 | 1.16 | 82.4 | 30.6 | 6.0 | 2.5 |
| Mean | 1379 | 36.7 | 4.6 | 1.14 | 82.8 | 30.6 | 6.1 | 2.4 |
| Cv | 5.9 | 2.6 | 5.6 | 2.3 | 1.2 | 3.6 | 4.8 | 17.0 |
| LSD .05 | 96 | 1.1 | 0.3 | 0.03 | 1.2 | 1.3 | 0.3 | 0.5 |
| Hartsville, SC - S6HVC427 | | | | | | | | |
| DP2379 | 1188 | 39.8 | 4.9 | 1.09 | 83.6 | 28.2 | 7.6 | |
| HS26 | 867 | 38.8 | 4.7 | 1.09 | 83.8 | 29.4 | 7.3 | |
| DP Acala 90 | 1359 | 42.1 | 4.7 | 1.15 | 84.0 | 30.8 | 6.5 | |
| Mean | 1308 | 41.9 | 4.7 | 1.14 | 84.6 | 29.8 | 6.8 | |
| Cv | 7 | 1.4 | 3.3 | 1.77 | 0.5 | 2.35 | 2.2 | |
| LSD .05 | 107 | 0.7 | 0.2 | 0.02 | 0.5 | 0.83 | 0.2 | |
| Three Location Summary | | | | | | | | |
| DP2379 | 1143 | 37.7 | 4.7 | 1.12 | 82.8 | 29.4 | 6.9 | 1.9 |
| HS26 | 935 | 36.2 | 4.6 | 1.13 | 83.4 | 30.5 | 6.7 | 1.5 |
| DP Acala 90 | 1262 | 37.3 | 4.5 | 1.16 | 82.7 | 30.3 | 6.2 | 2.8 |
| Mean | 1182 | 37.9 | 4.5 | 1.14 | 83.3 | 30.2 | 6.4 | 2.6 |
| Cv | 7.1 | 2.3 | 4.5 | 2.5 | 1.0 | 3.3 | 3.2 | 17.2 |
| LSD .05 | 58 | 0.6 | 0.1 | 0.02 | 0.6 | 0.7 | 0.1 | 0.4 |
| No. Reps | 12 | 12 | 12 | 12 | 12 | 12 | 12 | 8 |
| R-squared | 0.93 | 0.95 | 0.74 | 0.46 | 0.69 | 0.61 | 0.85 | 0.69 |

Mic — Micronaire
Len — Fiber length
UR — Uniformity ratio
T1 — Fiber strength
E1 — Fiber elongation
So — Stringout rating (1 = stormproof, 5 = loose, open boll)

TABLE 2

Comparison of DP 2379 vs Paymaster HS26 in the Stripper Growing Regions of Texas

| | Lint Yield | | | Gin Turnout | | | Maturity Rating | | | Storm Resistance | | |
|---|---|---|---|---|---|---|---|---|---|---|---|---|
| Year | DP 2379 | HS26 | Diff | DP 2379 | HS26 | Diff | DP 2379 | HS26 | Diff | DP 2379 | HS26 | Diff |
| 1993 | 1427 | 1247 | 180 | 24.2 | 21.8 | 2.4 | 3.7 | 4.0 | −0.3 | 2.0 | 2.0 | 0.0 |
| 1993 | 1030 | 919 | 111 | 25.6 | 23.5 | 2.1 | | | | 1.2 | 1.4 | −0.2 |
| 1993 | 1267 | 1060 | 207 | 24.4 | 22.2 | 2.2 | | | | 1.2 | 1.0 | 0.2 |
| 1994 | 1097 | 919 | 178 | 29.0 | 27.0 | 2.0 | | | | 2.3 | 2.0 | 0.3 |
| 1994 | 1291 | 1155 | 136 | 32.0 | 29.0 | 3.0 | | | | 1.7 | 2.0 | −0.3 |
| 1994 | 1439 | 1442 | −3 | 33.0 | 32.0 | 1.0 | | | | 2.0 | 2.3 | −0.3 |
| 1995 | 894 | 734 | 160 | 24.5 | 22.0 | 2.5 | 2.1 | 3.6 | −1.5 | 1.7 | 1.3 | 0.4 |
| 1995 | 945 | 782 | 163 | 22.8 | 20.7 | 2.1 | 4.9 | 4.9 | 0.0 | 1.3 | 1.7 | −0.4 |
| 1995 | 659 | 566 | 93 | 27.3 | 26.7 | 0.6 | | | | 2.0 | 1.7 | 0.3 |
| 1995 | 923 | 895 | 28 | 26.6 | 25.2 | 1.4 | 2.9 | 5.0 | −2.1 | 2.0 | 2.0 | 0.0 |
| 1995 | 1695 | 1476 | 219 | 30.0 | 27.9 | 2.1 | 4.2 | 5.0 | −0.8 | 1.7 | 1.7 | 0.0 |
| 1996 | 846 | 693 | 152 | 37.7 | 35.6 | 2.2 | 3.5 | 4.0 | −0.5 | 2.0 | 1.0 | 1.0 |
| 1996 | 1132 | 896 | 236 | 37.6 | 38.1 | −0.5 | | | | | | |
| Average difference | | | 143 | | | 1.8 | | | −0.9 | | | 0.1 |
| Number of tests | | | 13 | | | 13 | | | 6 | | | 12 |
| T-test probability | | | <0.001 | | | <0.001 | | | 0.021 | | | 0.238 |

| | Micronaire | | | Length | | | Uniformity Ratio | | | T1 Strength | | | E1 Elongation | | |
|---|---|---|---|---|---|---|---|---|---|---|---|---|---|---|---|
| Year | DP 2379 | HS26 | Diff | DP 2379 | HS26 | Diff | DP 2379 | HS26 | Diff | DP 2379 | HS26 | Diff | DP 2379 | HS26 | Diff |
| 1993 | 3.3 | 3.2 | 0.1 | 1.07 | 1.07 | 0.00 | 82.1 | 82.8 | −0.7 | 31.5 | 30.3 | 1.2 | 8.8 | 8.7 | 0.1 |
| 1993 | 3.5 | 3.5 | 0.0 | 1.03 | 1.04 | −.01 | 81.9 | 82.4 | −0.5 | 31.0 | 29.8 | 1.2 | 8.7 | 8.7 | 0.0 |
| 1993 | 3.3 | 3.4 | −0.1 | 1.07 | 1.09 | −.02 | 82.3 | 83.1 | −0.8 | 31.5 | 32.2 | −0.7 | 10.5 | 10.2 | 0.3 |
| 1994 | 3.7 | 3.1 | 0.6 | 1.07 | 1.09 | −.02 | 83.0 | 83.0 | 0.0 | 32.1 | 29.5 | 2.6 | 9.4 | 8.8 | 0.6 |
| 1994 | 4.0 | 4.1 | −0.1 | 1.08 | 1.11 | −.03 | 84.0 | 85.0 | −1.0 | 30.2 | 32.9 | −2.7 | 9.3 | 9.2 | 0.1 |
| 1994 | 3.8 | 4.4 | −0.6 | 1.06 | 1.07 | −.01 | 83.0 | 84.0 | −1.0 | 31.4 | 31.4 | 0.0 | 8.9 | 9.0 | −0.1 |
| 1995 | 4.0 | 4.4 | −0.4 | 1.06 | 1.12 | −.06 | 82.0 | 84.0 | −2.0 | 32.0 | 29.7 | 2.3 | 10.4 | 11.6 | −1.2 |
| 1995 | 3.6 | 3.8 | −0.2 | 1.07 | 1.08 | −.01 | 82.0 | 82.0 | 0.0 | 29.1 | 31.7 | −2.6 | 10.8 | 10.8 | 0.0 |
| 1995 | 4.7 | 4.6 | 0.1 | 0.99 | 0.94 | 0.05 | 83.0 | 82.0 | 1.0 | 29.0 | 30.0 | −1.0 | 8.4 | 8.0 | 0.4 |
| 1995 | 3.9 | 3.5 | 0.4 | 1.04 | 1.05 | −.01 | 81.0 | 81.0 | 0.0 | 31.3 | 34.1 | −2.8 | 10.2 | 11.2 | −1.0 |
| 1995 | 4.4 | 4.2 | 0.2 | 1.09 | 1.11 | −.02 | 84.0 | 84.0 | 0.0 | 32.5 | 32.5 | 0.0 | 9.7 | 10.0 | −0.3 |
| 1996 | 4.1 | 4.1 | 0.0 | 1.07 | 1.07 | 0.00 | 82.8 | 82.4 | 0.4 | 30.1 | 30.9 | −0.8 | 7.6 | 7.9 | −0.3 |
| 1996 | 4.3 | 4.1 | 0.1 | 1.12 | 1.11 | 0.01 | 83.0 | 84.0 | −1.0 | 29.4 | 30.6 | −1.2 | 7.2 | 7.1 | 0.2 |
| Average Diff. | | | 0.0 | | | −.01 | | | −0.4 | | | −0.4 | | | −0.1 |
| Number of tests | | | 13 | | | 13 | | | 13 | | | 13 | | | 13 |
| T-test probability | | | .468 | | | .099 | | | .033 | | | .247 | | | .255 |

TABLE 3

Seed Weight Comparisons

| Region | Year | 100 Seed Weight | | | 100 Seed Weight | | |
|---|---|---|---|---|---|---|---|
| | | DP 2379 | HS26 | Diff | DP 2379 | DP90 | Diff |
| HP | 1996 | 10.3 | 10.7 | -0.4 | | | |
| HP | 1996 | 11.0 | 12.2 | -1.2 | | | |
| MS | 1996 | 11.2 | 12.0 | -0.8 | 11.2 | 9.8 | 1.4 |
| AZ | 1996 | 10.6 | 11.0 | -0.4 | 10.6 | 9.2 | 1.4 |
| Average Difference | | | | -0.7 | | | 1.4 |
| Number of tests | | | | 4 | | | 2 |
| T-test probability | | | | .018 | | | <.001 |

TABLE 4

PVP Test - Scott, MS - 1996 - 6SMC138*

| Name | Lint % | 100 Sdwt | Lint Index | Lint/boll | Seeds/boll | Seed Cotton/boll |
|---|---|---|---|---|---|---|
| DP2379 | 36.8 | 11.5 | 6.84 | 1.97 | 29.1 | 5.36 |
| DP Acala 90 | 36.3 | 9.8 | 5.63 | 1.78 | 31.2 | 4.91 |
| HS26 | 37.0 | 11.9 | 6.95 | 2.07 | 28.9 | 5.58 |
| Mean | 37.1 | 9.7 | 5.81 | 1.73 | 29.9 | 4.67 |
| Cv | 2.1 | 3.5 | 4.1 | 5.5 | 5.1 | 5.3 |
| LSD .05 | 0.9 | 0.4 | 0.28 | 0.11 | 1.8 | 0.29 |
| R-squared | 0.85 | 0.90 | 0.86 | 0.75 | 0.60 | 0.79 |

*Hand picked boll samples

TABLE 5

PVP Trial –1996 Three Location Summary Scott, MS; Casa Grande, AZ; Hartsville, SC

A

| Entry | Height | Total Nodes | Vegetative Nodes | Fruiting Nodes | HNR | Bolls per Plant |
|---|---|---|---|---|---|---|
| DP Acala 90 | 96.9 | 21.6 | 4.9 | 16.8 | 1.8 | 14.1 |
| DP 2379 | 91.6 | 20.6 | 4.4 | 16.2 | 1.8 | 12.8 |
| HS 26 | 86.2 | 19.4 | 4.4 | 15.0 | 1.8 | 12.0 |
| Mean | 94.5 | 20.3 | 4.7 | 15.6 | 1.9 | 13.9 |
| Probability (paired t of DP 2379 vs. DP90) | 0.1574 | 0.1592 | 0.1614 | 0.2774 | 0.4749 | 0.1579 |
| Probability (paired t of DP 2379 vs. HS26) | 0.0436 | 0.0234 | 0.3705 | 0.0024 | 0.4221 | 0.2698 |

B

| | % Bolls by Position | | | # of Nodes | % FP1 Retention | | | Date of |
| Entry | FP1 | FP2 | >FP2 | Vegetative | 95% Zone | Bottom 5 | 95% Zone | FBCB | 50% Open |
|---|---|---|---|---|---|---|---|---|---|
| DP Acala 90 | 55.8 | 31.8 | 5.3 | 7.0 | 18.0 | 50.0 | 59.7 | 10.3 | 22-Aug |
| DP 2379 | 59.5 | 27.5 | 5.4 | 7.6 | 15.9 | 63.9 | 64.0 | 9.4 | 20-Aug |
| HS 26 | 61.4 | 27.2 | 5.4 | 6.0 | 16.0 | 59.3 | 64.6 | 8.9 | 22-Aug |
| Mean | 56.3 | 27.4 | 6.5 | 9.8 | 16.6 | 60.5 | 61.7 | 8.7 | 23-Aug |
| Probability (paired t of DP 2379 vs. DP90) | 0.2553 | 0.1574 | 0.4984 | 0.1856 | 0.0780 | 0.1502 | 0.2472 | 0.0717 | 0.1678 |
| Probability (paired t of DP 2379 vs. HS26) | 0.2627 | 0.4080 | 0.4919 | 0.0128 | 0.3553 | 0.0648 | 0.4307 | 0.1908 | 0.009 |

DEPOSIT INFORMATION

A deposit of the Delta and Pine Land Company cotton cultivar DP 2379 disclosed above and recited in the appended claims has been made with the American Type Culture Collection (ATCC), 10801 University Boulevard, Manassas, Va. 20110. The date of deposit was Jul. 30, 1999. The deposit of 2,500 seeds were taken from the same deposit maintained by Delta and Pine Land Company since prior to the filing date of this application. All resrtictions upon the deposit have been removed, and the deposit is intended to meet all of the requirements of 37 C.F.R. §1.801–1.809. The ATCC accession number is PTA-442. The deposit will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A cotton cultivar seed designated DP 2379 having ATCC Accession No. PTA-442.

2. A plant or its parts, each produced by growing the seed of claim 1.

3. Pollen of the plant of claim 2.

4. An ovule of the plant of claim 2.

5. A cotton plant having all of the physiological and morphological characteristics of the plant of claim 2.

6. Tissue culture of the plant of claim 2.

7. A cotton plant regenerated from the tissue culture of claim 6, said plant having all the physiological and morphological characteristics of the plant of claim 2.

8. A method for producing a cotton cultivar seed comprising crossing a first cultivar parent cotton plant with a second cultivar parent cotton plant and harvesting the resultant cultivar cotton seed, wherein said first or second parent cotton plant is the cotton plant of claim 2.

9. A hybrid seed produced by the method of claim 8.

10. A hybrid plant or its parts, each produced by growing said hybrid cotton seed of claim 9.

11. Seed produced from said hybrid plant of claim 10.

12. A method for producing a hybrid cotton seed comprising crossing a plant according to claim 2 with another, different cotton plant.

13. A hybrid seed produced by the method of claim 12.

14. A hybrid plant or its parts, each produced by growing said hybrid cotton seed of claim 13.

15. Seed produced from said hybrid plant of claim 14.

* * * * *